US008292961B2

(12) United States Patent
Osman

(10) Patent No.: US 8,292,961 B2
(45) Date of Patent: Oct. 23, 2012

(54) BIOLOGIC VERTEBRAL RECONSTRUCTION

(76) Inventor: Said G. Osman, Russellville, AL (US)

( * ) Notice: Subject to any disclaimer, the term of this patent is extended or adjusted under 35 U.S.C. 154(b) by 644 days.

(21) Appl. No.: 12/018,507

(22) Filed: Jan. 23, 2008

(65) Prior Publication Data
US 2009/0187249 A1 Jul. 23, 2009

(51) Int. Cl.
*A61F 2/44* (2006.01)
(52) U.S. Cl. ................................. 623/17.12
(58) Field of Classification Search .... 623/17.11–17.14, 623/1.11, 17.15–17.16; 606/262, 76, 77, 606/78, 90; 604/96.01, 101.04, 102.01, 102, 604/3, 103, 103.06–103.09
See application file for complete search history.

(56) References Cited

U.S. PATENT DOCUMENTS

| | | | | |
|---|---|---|---|---|
| 2002/0147497 | A1* | 10/2002 | Belef et al. | 623/17.12 |
| 2003/0199984 | A1* | 10/2003 | Trieu | 623/17.16 |
| 2004/0210231 | A1* | 10/2004 | Boucher et al. | 606/93 |
| 2005/0261781 | A1* | 11/2005 | Sennett et al. | 623/23.54 |
| 2009/0105823 | A1* | 4/2009 | Williams et al. | 623/17.16 |

* cited by examiner

*Primary Examiner* — Eduardo C Robert
*Assistant Examiner* — Summer Kostelnik
(74) *Attorney, Agent, or Firm* — Nixon & Vanderhye P.C.

(57) ABSTRACT

A device and method for biologic vertebral reconstruction utilizes a biologically active jacket inserted into a cavity formed in a vertebra to be reconstructed. An artificial bone material is inserted into the biologically active jacket and allowed to set. The structure and method described herein provide for effective biologic vertebral reconstruction. The use of a biological material and artificial bone enables the host bone to replace the artificial bone over a period of time. Additionally, the structure of the biologically active jacket minimizes any impact into the spinal canal and the paravertebral spaces. Moreover, because of its biomechanical characteristics, which approximate the host bone, there is relative protection of the neighboring vertebral against fracture. Still further, the materials of the biologically active jacket may be impregnated with various substances to achieve various advantageous tasks.

8 Claims, 6 Drawing Sheets

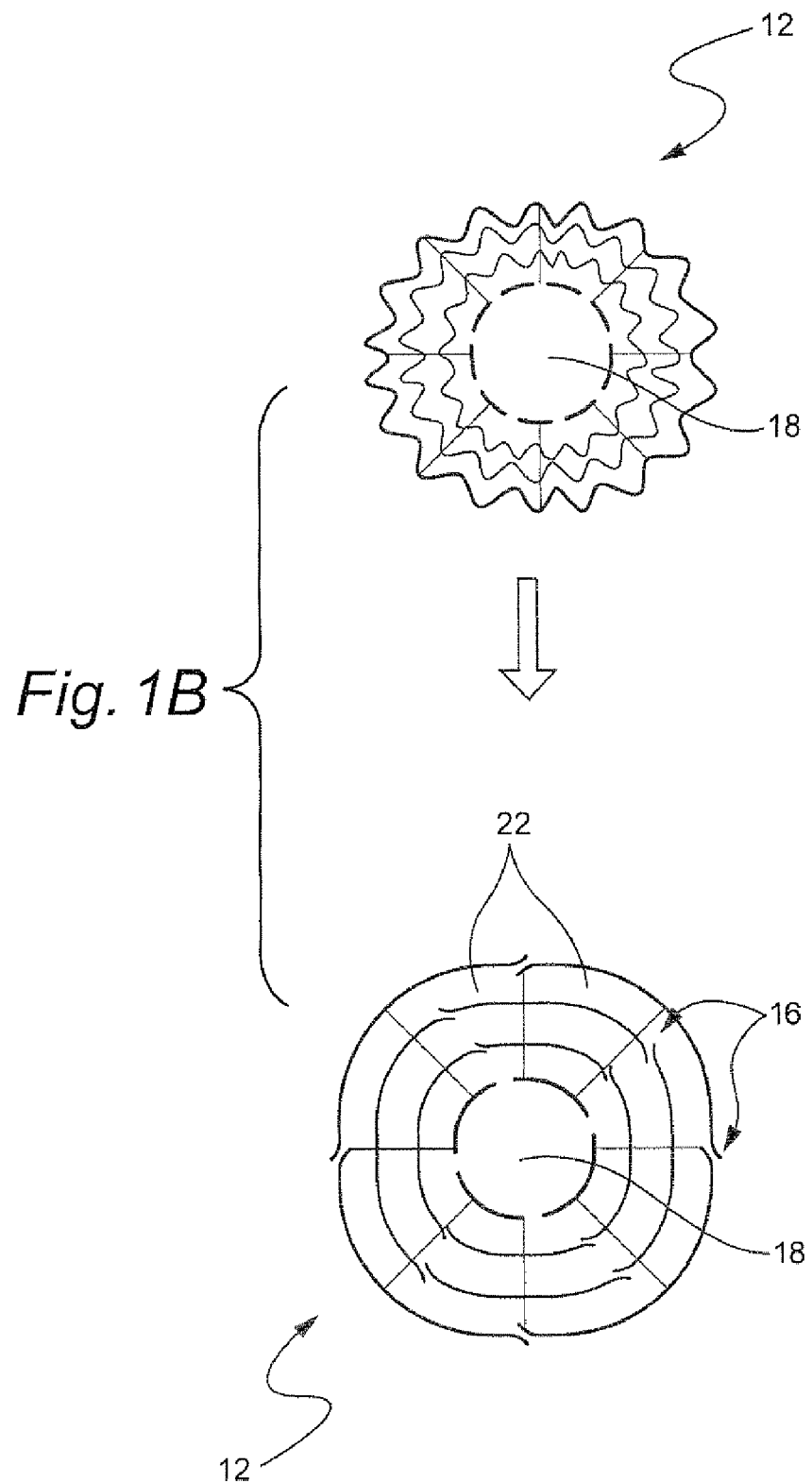

BIOLOGIC VERTEBRAL RECONSTRUCTION

CROSS-REFERENCES TO RELATED APPLICATIONS (NOT APPLICABLE)

STATEMENT REGARDING FEDERALLY SPONSORED RESEARCH OR DEVELOPMENT (NOT APPLICABLE)

BACKGROUND OF THE INVENTION

The invention relates to biologic vertebral reconstruction and, more particularly, to devices and methods for biologic vertebral reconstruction utilizing a biologically active jacket inserted into a cavity formed in a vertebra to be reconstructed.

Vertebral compression fractures are quite common in the elderly population. These fractures occur following minor injuries or spontaneously in the elderly osteoporotic spine. The other group of patients, usually middle aged, is those on long term steroid therapy for conditions such as chronic obstructive pulmonary disease. In the younger population with normal bone mineralization, vertebral fractures usually occur following high energy injuries such as motor vehicle accidents or a fall from heights.

Until recently, the elderly osteoporotic fractures were treated with pain control and bracing, depending on the severity of pain. However, over the last decade, there has been increasing use of minimally invasive procedures such as vertebroplasty and Kyphoplasty, whereby bone cement in a state of low viscosity is injected into the fractured vertebrae. As the bone cement sets it glues together the fragments of the fractured vertebra. Patients usually wake up from anesthesia with minimal discomfort.

As the use of this technique became more common, some adverse effects of the treatment have become apparent. At the time of surgery, patients may suffer from cardio-respiratory failure associated from infusion of large amounts of polymethylmethacrylate monomers into the circulation; in the case of vertebroplasty which requires injection of the cement at high pressures, extrusion of the cement into the venous channels and embolization into the pulmonary veins have been described; the cement may extrude through the cracks in the vertebrae into the spinal canal and compress the spinal cord or the spinal nerves with possible serious complications.

It is now being appreciated by surgeons that reinforcing an osteoporotic vertebra with bone cement may lead to fractures of the adjacent vertebra by compression against a very much hardened neighboring vertebra. The other concern is the fact that the bone cement will stay permanently in the vertebra because it is not resorbable. The long term consequence of this is not known, hence, its use is generally avoided in young vertebral fractures.

Treatments of young vertebral fractures are either conservative or surgical. The conservative approach is usually favored when the deformity of the vertebra is not severe and when there is no injury to neural elements. However, the biomechanical alterations caused even by an apparently minor deformity may lead to the development of chronic back pain. Surgical stabilization becomes imperative if there is spinal cord injury, usually associated with significant instability of the spine. The stabilization surgery usually involves massive surgical trauma through either or both anterior and posterior approaches.

BRIEF SUMMARY OF THE INVENTION

Significant aspects of the described embodiments include: (a) the technology involves implantation of a biologic material—artificial bone into the fractured vertebra such that the host bone will replace the artificial bone over a period of time making this a more suitable option than the currently used bone cement; (b) the implant is inserted into the vertebra in a biologically active jacket, to minimize its extrusion into the spinal canal and the paravertebral spaces; (c) because of its biomechanical characteristics, which approximate the host bone, there is relative protection of the neighboring vertebrae against fracture; and (d) the walls of the implant jacket may be impregnated with various substances to achieve various advantageous tasks. Examples of these include bone morphogenic proteins to stimulate incorporation of the artificial bone into the host bone, among others.

In an exemplary embodiment, a method of biologic vertebral reconstruction includes the steps of (a) forming a cavity in a vertebra to be reconstructed; (b) inserting a biologically active jacket in the cavity; and (c) injecting an artificial bone material into the biologically active jacket and allowing the artificial bone material to set. Step (a) may be practiced by drilling. In this context, the method may further include a step of collecting bone shavings during the drilling step. Preferably, step (a) is practiced by drilling in the vertebra to within five millimeters of the vertebra anterior cortex.

Prior to step (b), the method may include impregnating the biologically active jacket with a predetermined substance. The impregnating step may include impregnating the biologically active jacket with a catalyst to speed up the setting of the artificial bone material injected in step (c). Alternatively, the impregnating step may include impregnating the biologically active jacket with a bone morphogenic protein to stimulate incorporation of the artificial bone material into the vertebra to be reconstructed. As still another alternative, the impregnating step may include impregnating the biologically active jacket with an antibiotic as a prophylaxis against infection.

Prior to step (a), the method may include steps of inserting a trochar and a cannula into a target pedicle of the vertebra to be reconstructed, and removing the trochar, where step (a) is practiced by inserting a drilling tool through the cannula, drilling the cavity, and removing the drilling tool. In this context, step (b) may be practiced by inserting the biologically active jacket in the cavity through the cannula.

In another exemplary embodiment, a tool kit for performing biologic vertebral reconstruction, includes a drilling tool including a drill bit for forming a cavity in a vertebra to be reconstructed, and a biologically active jacket sized for insertion into the cavity. An artificial bone injector is attachable to the biologically active jacket. Additionally, an artificial bone material is injectable into the biologically active jacket by the artificial bone injector. The drilling tool may include a biopsy tool attachment for collecting bone shavings during drilling for a biopsy specimen. Preferably, the biologically active jacket is formed of various bioabsorbable synthetic materials.

In still another exemplary embodiment, a biologically active jacket for use in a biologic vertebral reconstruction includes expandable jacket walls and is sized for insertion into a cavity formed in a vertebra to be reconstructed. The biologically active jacket is formed of various bioabsorbable synthetic materials. For example, the biologically active jacket may be formed of polyglycolic acid. Generally, the biologically active jacket may be formed of a synthetic bioabsorbable woven fiber network. In one arrangement, the biologically active jacket is multi-loculated, where loculations include connecting valves made of overlapping wall fibers. The jacket walls may be formed as one of single layer, double layer, uni-compartmental, multi-compartmental, elastic, inelastic, etc.

The jacket may also be provided with a central fenestrated channel. In this context, the central fenestrated channel may be sealed at one end and may include a threaded connection at an opposite end, the threaded connection being configured to receive a cement injector. The jacket may additionally include concentric chambers disposed surrounding the central fenestrated channel, where each of the concentric chambers is partially loculated.

BRIEF DESCRIPTION OF THE DRAWINGS

These and other aspects and advantages will be described in detail with reference to the accompanying drawings, in which:

FIGS. 1A and 1B show a longitudinal section view and a transverse section view of a biologically active jacket, respectively;

DETAILED DESCRIPTION

Figure 1A:
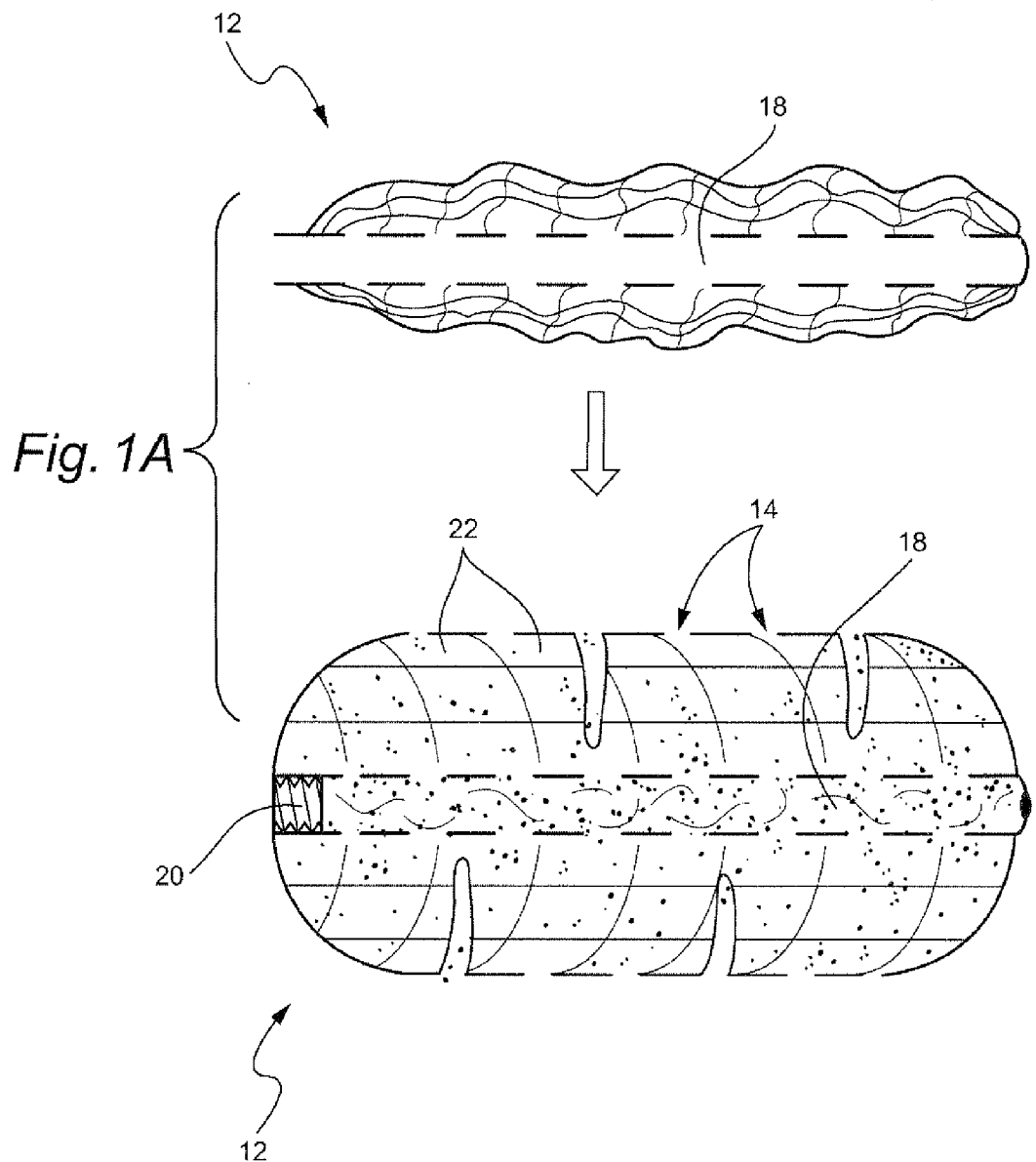

With reference to FIGS. 1A and 1B, a preferred embodiment includes a jacket 12 of synthetic bio-absorbable fiber network woven like cloth and may be uni-compartmental or multi-loculated. If multi-loculated the loculations 14 will have connecting valves 16 made of overlapping wall fibers acting as trap-doors that open up as the chamber is filled with artificial bone to allow filling of the neighboring chambers. The jacket 12 has a central fenestrated channel 18 that runs through the length of the jacket 12. The channel 18 is sealed at its far end, and the near end is threaded 20 to allow a cement injector to be screwed on.

The multi-loculated design has concentric chambers with the central channel 18 running down the center of the innermost chamber. Each chamber may be partially loculated to reinforce the construct with multiple networks of fibers to minimize the risk of compression fracture of the implant itself. The artificial bone is injected into the central channel 18 from which the cement extrudes into the inner-most chamber. As the chamber 18 fills up, its wall stretches out to open up the valves 16 in its outer wall, which then fill up with the artificial bone, from the inner chamber, to open the valves in its outer wall, so on and so forth until all the chambers are full. The outer chambers 22 will also have fenestrations in the outer wall to allow some artificial bone to extrude and anchor into the host bone. The entire jacket 12 may be fitted with a network of channels extending into its interior from the outer wall. These channels will act as a conduit for vascular ingrowth.

The fiber network of the jacket 12 may be used as a carrier for various factors by impregnating with a material suited for a particular purpose. For example, the material may be bone morphogenic proteins to stimulate osteo-induction and osteo-synthesis within the artificial bone, antibiotics as a prophylaxis against infection, or the like.

The artificial bone 24 (FIG. 3), in a preferred embodiment, is in a semi-liquid state which sets into a hard bone within a few minutes after injection into the implant jacket 12 in the vertebral body. A catalyst may also be impregnated into the walls of the jacket 12 to speed up the setting process. The ceramic bone (artificial bone) 24 may be made out of hydroxyapatite or other calcium compounds.

Figure 2:
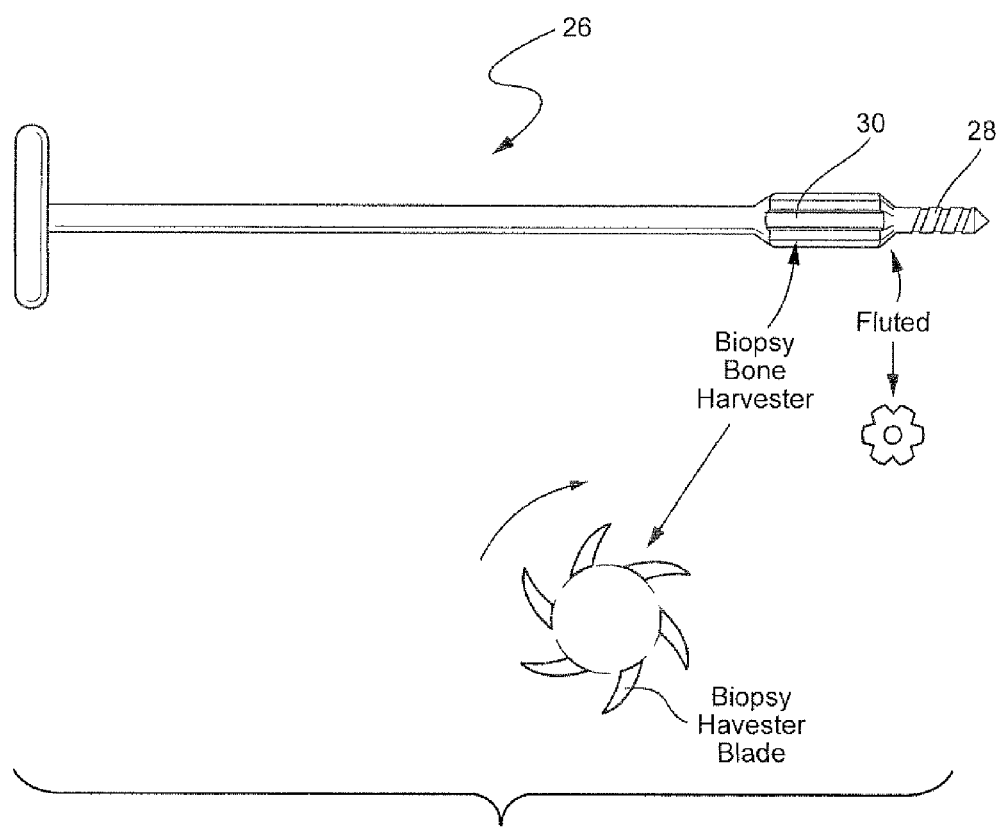
FIG. 2 illustrates a drill and biopsy tool.

FIG. 2 illustrates a drill and biopsy tool 26 for creating a cavity in the vertebra to be reconstructed and for taking a biopsy sample. The device 26 includes a drill bit 28 at the tip, and immediately next to it is biopsy tool 30 for shaving of the host bone. The shaving tool 30 is hollow in its center for collection of bone shavings. At the conclusion of the drilling, enough bone shavings will have been collected for a biopsy specimen. The diameter of the shaving tool 30 is the same or slightly larger than the diameter of the unexpanded implant jacket 12.

Figure 3:
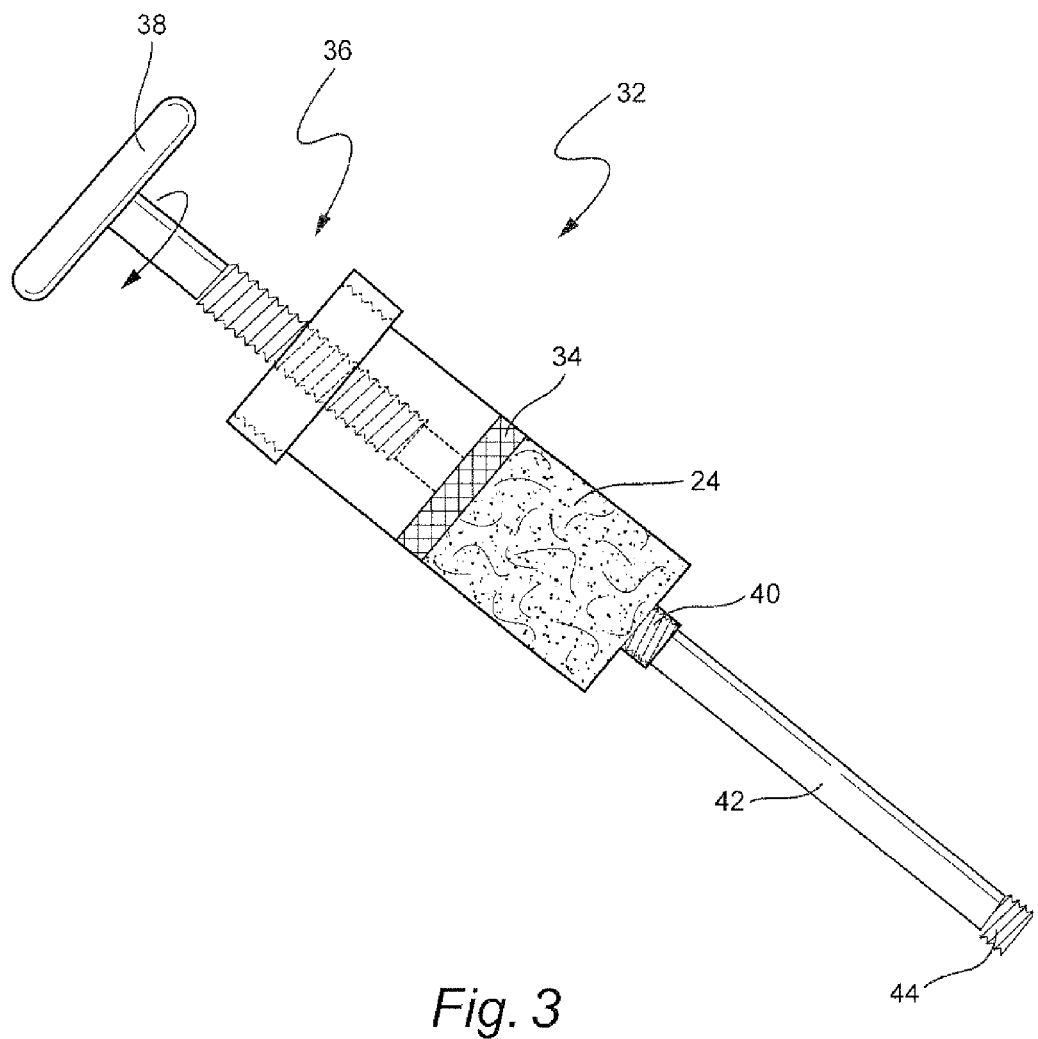
FIG. 3 illustrates an artificial bone injector.
Figure 4:
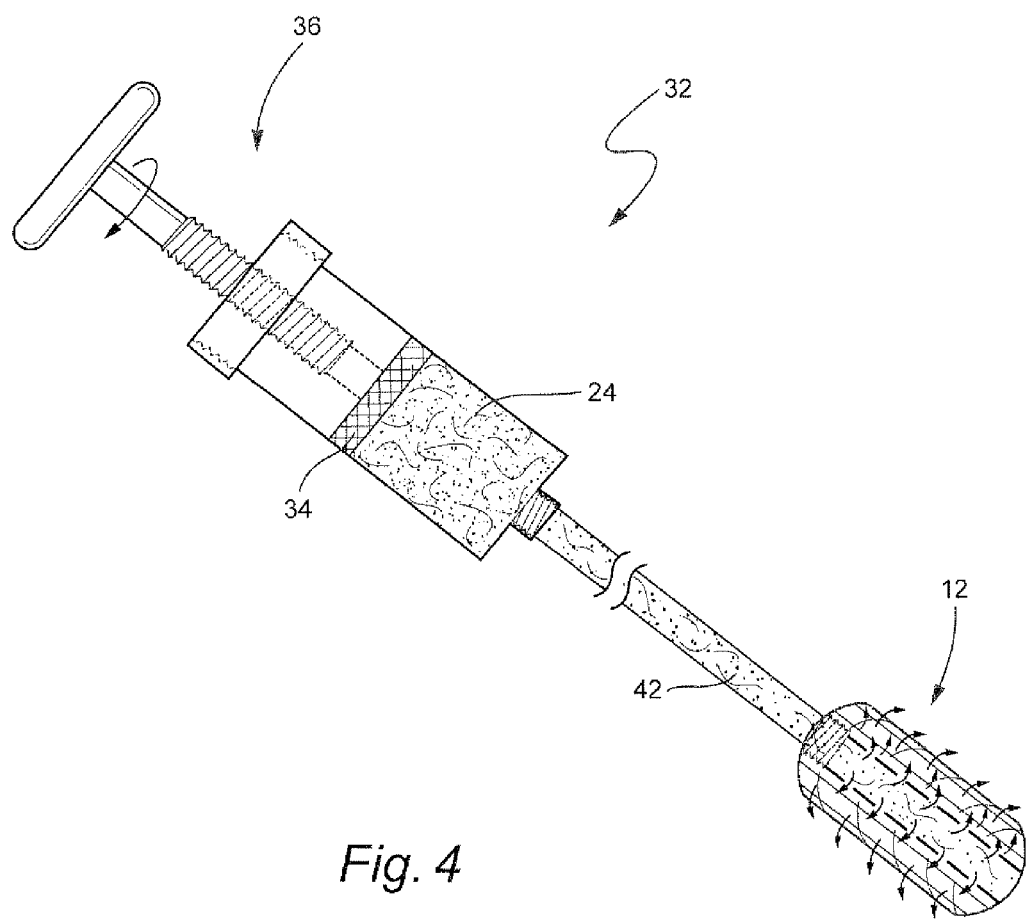
FIG. 4 illustrates the artificial bone injector coupled with the biologically active jacket.

The artificial bone injector 32 is shown in FIGS. 3 and 4. The injector 32 includes a syringe with a plunger 34 that is operated by a screw mechanism 36. As the handle 38 is turned clockwise, the plunger 34 goes deeper into the syringe and pushes out the artificial bone 24. The nozzle 40 of the syringe is connected through a screw mechanism to an injection cannula 42. The injection cannula 42 in turn includes a threaded connector 44 or the like that is engageable with the threads 20 on the biologically active jacket 12.

Figure 5A:
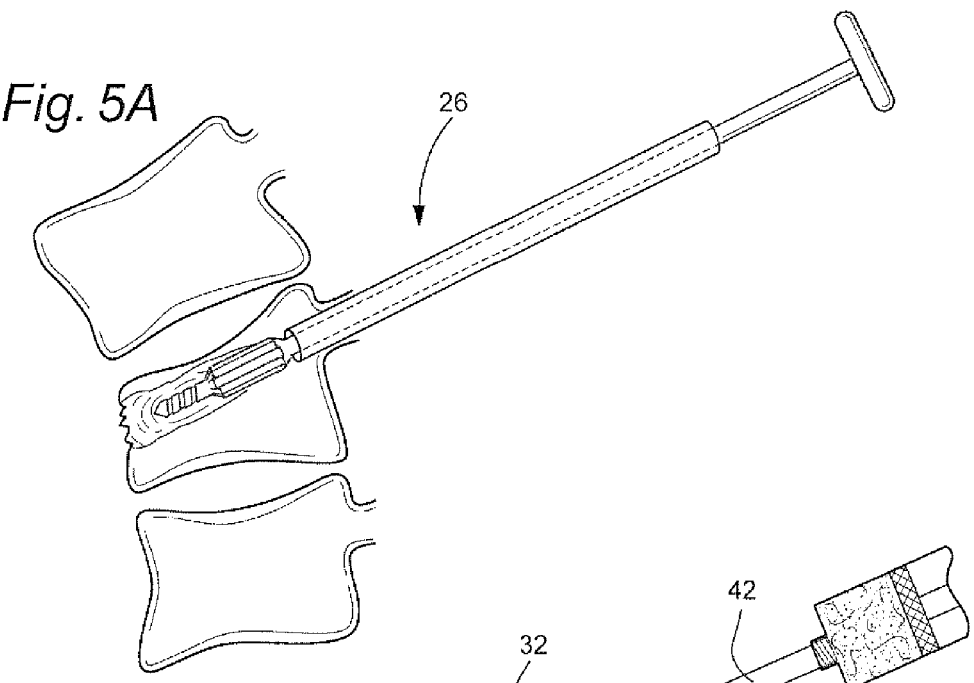
FIGS. 5A-5C illustrate the steps in the vertebral reconstruction.
Figure 5B:
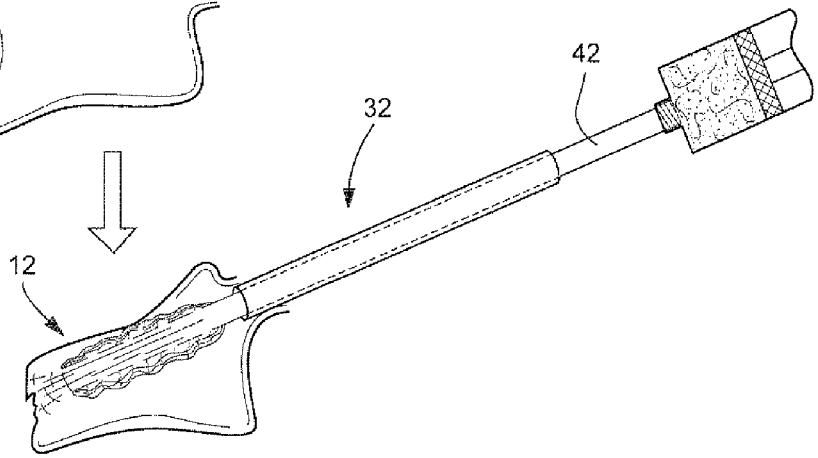
Figure 5C:
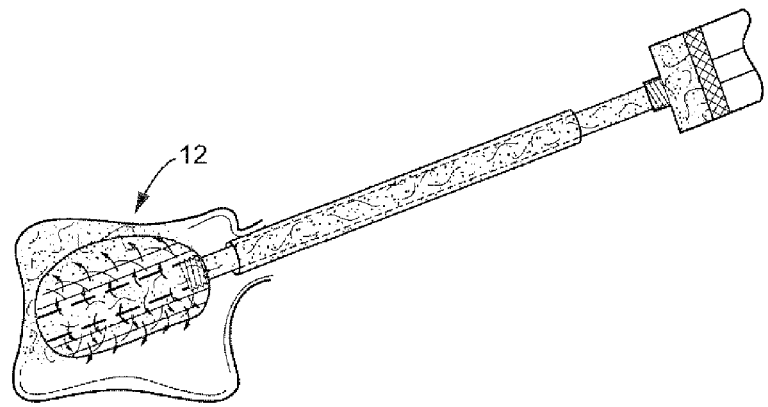

The process of biologic vertebral reconstruction will be described with reference to FIGS. 5A-5C.

The patient is placed on a radiolucent operating table in the prone or lateral position depending on the surgeon's preference. The skin is marked at the level of the target pedicles with the aid of fluoroscopic visualization. Through a small skin incision, a trochar and cannula are inserted under fluoroscopic visualization into the target pedicle. The position is checked in antero-posterior, lateral and oblique projections. The trochar is then inserted deeper into the vertebra to establish the preferred trajectory. The cannula 42 is then advanced until it is at least 3 mm deep to the posterior wall of the vertebra to be reconstructed. At this point, the trochar is removed leaving the cannula 42 in place.

The drill/biopsy tool 26 is inserted through the cannula, and hand drilling is performed by clockwise turning of the handle. See FIG. 5A. Drilling is carried out to within 5 millimeters of the anterior cortex. The drill/biopsy tool 26 is then removed.

Subsequently, the unexpanded implant jacket 12 is attached to the injection cannula 42 and is inserted through the cannula 42 to the appropriate depth as determined by fluoroscopically reading the position of the radio-opaque marker at the advancing tip of the device. See FIG. 5B.

The injection cannula 42 is attached to the syringe containing the artificial bone, and the artificial bone is injected while visualizing fluoroscopically. See FIG. 5C.

Exemplary characteristics and properties of the device construction are outlined below.

1. Implant jacket:
   a. Material—polymer of various bioabsorbable synthetic materials such as polyglycolic acid
   b. Wall design
      i. Single layer
      ii. Double layer wall
      iii. Uni-compartmental
      iv. Multi-compartmental
      v. Elastic
      vi. In-elastic, folded
   c. Implantation mechanism
      i. Create void and then implant
      ii. Implant to correct deformity as the artificial bone is injected
   d. Filling mechanism 2. Artificial bone
  a. Ceramic
  b. Host bone
  c. Host or ceramic impregnated with radio-opaque material for better visualization intra-operatively.
3. Instruments
  a. Drill/biopsy tool
  b. Artificial bone injection device
4. Technique
  a. Prep
  b. Insertion of jacket
  c. Implantation of the artificial bone The structure and method described herein provide for effective biologic vertebral reconstruction. The use of a biological material and artificial bone enables the host bone to replace the artificial bone over a period of time. Additionally, the structure of the biologically active jacket minimizes any impact into the spinal canal and the paravertebral spaces. Moreover, because of its biomechanical characteristics, which approximate the host bone, there is relative protection of the neighboring vertebra against fracture. Still further, the materials of the biologically active jacket may be impregnated with various substances to achieve various advantageous tasks.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A biologically active jacket for use in a biologic vertebral reconstruction, the biologically active jacket comprising:
  a fenestrated jacket wall for insertion into a cavity formed in a vertebra to be reconstructed, the jacket wall being expandable and defining an interior cavity;
  a central fenestrated channel disposed in the interior cavity and extending through the jacket wall; and
  concentric chambers disposed surrounding the central fenestrated channel, wherein each of the concentric chambers is partially loculated,
  wherein the biologically active jacket is formed of various bioabsorbable synthetic materials, and wherein the central fenestrated channel is sealed at one end and includes an internal threaded connection at an opposite end, the internal threaded connection being structured and positioned to receive a cement injector.

2. A biologically active jacket according to claim 1, wherein the biologically active jacket is formed of polyglycolic acid.

3. A biologically active jacket according to claim 1, wherein the biologically active jacket is formed of a synthetic bioabsorbable woven fiber network.

4. A biologically active jacket according to claim 1, wherein the biologically active jacket is multi-loculated, and wherein loculations comprise connecting valves made of overlapping wall fibers.

5. A biologically active jacket according to claim 1, wherein the jacket walls are formed as one of single layer, double layer, uni-compartmental, multi-compartmental, elastic, and inelastic.

6. A biologically active jacket comprising:
  a fenestrated jacket wall for insertion into a cavity formed in a vertebra to be reconstructed, the jacket wall being expandable and defining an interior cavity;
  a central fenestrated channel disposed in the interior cavity and extending through the jacket wall; and
  a plurality of concentric chambers emanating from and surrounding the central fenestrated channel and extending between the central fenestrated channel and the fenestrated jacket wall, wherein each of the concentric chambers is partially loculated,
  wherein the biologically active jacket is formed of various bioabsorbable synthetic materials, and wherein the central fenestrated channel is sealed at one end and includes a threaded connection at an opposite end, the threaded connection being structured and positioned to receive a cement injector.

7. A biologically active jacket according to claim 6, wherein the biologically active jacket is formed of polyglycolic acid.

8. A biologically active jacket according to claim 6, wherein the biologically active jacket is formed of a synthetic bioabsorbable woven fiber network.

\* \* \* \* \*